(12) United States Patent
Tamura et al.

(10) Patent No.: US 10,769,822 B2
(45) Date of Patent: Sep. 8, 2020

(54) X-RAY CT APPARATUS

(71) Applicant: CANON MEDICAL SYSTEMS CORPORATION, Otawara-shi (JP)

(72) Inventors: Emi Tamura, Yokohama (JP); Hiroaki Nakai, Nasushiobara (JP)

(73) Assignee: CANON MEDICAL SYSTEMS CORPORATION, Otawara-shi (JP)

( * ) Notice: Subject to any disclaimer, the term of this patent is extended or adjusted under 35 U.S.C. 154(b) by 181 days.

(21) Appl. No.: 15/951,693

(22) Filed: Apr. 12, 2018

(65) Prior Publication Data

US 2018/0300909 A1     Oct. 18, 2018

(30) Foreign Application Priority Data

Apr. 13, 2017  (JP) .................................. 2017-079701
Apr. 10, 2018  (JP) .................................. 2018-075586

(51) Int. Cl.

| G06K 9/00 | (2006.01) |
| G06T 11/00 | (2006.01) |
| G01T 1/29 | (2006.01) |
| A61B 6/00 | (2006.01) |
| A61B 6/03 | (2006.01) |

(Continued)

(52) U.S. Cl.
CPC ............ *G06T 11/008* (2013.01); *A61B 6/032* (2013.01); *A61B 6/4241* (2013.01); *A61B 6/4266* (2013.01); *A61B 6/5205* (2013.01); *G01T 1/2985* (2013.01); *G06T 5/50* (2013.01);

(Continued)

(58) Field of Classification Search
CPC ......... A61B 6/032; A61B 6/4241; A61B 6/03; A61B 6/4266; G06T 2207/10081; G06T 11/005; G06T 7/136; G06K 9/60
See application file for complete search history.

(56) References Cited

U.S. PATENT DOCUMENTS 9,851,460 B1 * 12/2017 Rodrigues ............... G01T 1/247
10,452,948 B2 * 10/2019 Li ........................ A61B 6/5217
(Continued)

FOREIGN PATENT DOCUMENTS

JP    2015-033581    2/2015

OTHER PUBLICATIONS

Shikhaliev, Polad M. "Photon counting spectral CT: improved material decomposition with K-edge-filtered x-rays." Physics in Medicine & Biology 57.6 (2012): 1595. (Year: 2012).*

(Continued)

*Primary Examiner* — Li Liu
(74) *Attorney, Agent, or Firm* — Oblon, McClelland, Maier & Neustadt, L.L.P.

(57) ABSTRACT

An X-ray CT apparatus according to an embodiment includes a photon counting detector, and processing circuitry. The photon counting detector includes a plurality of detecting elements each of which outputs signals corresponding to numbers of photons that are counted. The processing circuitry generates pieces of first projection data on a basis of the signals from the plurality of detecting elements. The processing circuitry generate second projection data by bundling together, in spatial units, pieces of first projection data from a predetermined number of detecting elements among the plurality of detecting elements. The processing circuitry reconstructs a material decomposition image on a basis of the second projection data.

18 Claims, 9 Drawing Sheets

(51) Int. Cl.
*G06T 5/50* (2006.01)
*G06T 7/00* (2017.01)

(52) U.S. Cl.
CPC .. *G06T 7/0012* (2013.01); *G06T 2207/10081* (2013.01); *G06T 2207/30004* (2013.01)

(56) References Cited

U.S. PATENT DOCUMENTS

| | | | |
|---|---|---|---|
| 2007/0189443 A1* | 8/2007 | Walter | A61B 6/032 378/4 |
| 2015/0043795 A1 | 2/2015 | Rigie et al. | |
| 2015/0168570 A1* | 6/2015 | Pelc | G01T 1/247 378/5 |
| 2015/0178958 A1 | 6/2015 | Zou | |
| 2016/0054453 A1* | 2/2016 | Moriyasu | G01N 23/087 378/19 |
| 2016/0058404 A1* | 3/2016 | Nitta | A61B 6/4241 378/5 |
| 2017/0224299 A1* | 8/2017 | Petschke | A61B 6/5211 |

OTHER PUBLICATIONS

Taguchi, Katsuyuki, et al. "Image-domain material decomposition using photon-counting CT." Medical Imaging 2007: Physics of Medical Imaging. vol. 6510. International Society for Optics and Photonics, 2007. (Year: 2007).*

* cited by examiner

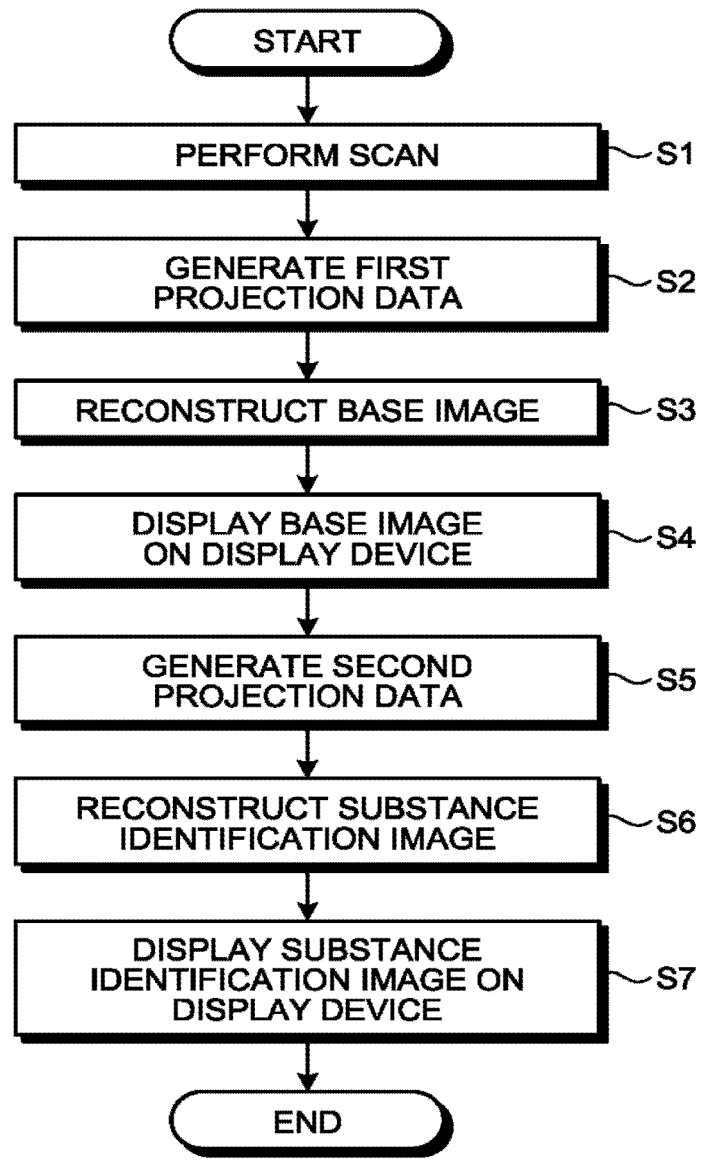

FIG.4A

CHANNEL DIRECTION →

ROW DIRECTION ↓

| r1c1 | r1c2 | r1c3 | r1c4 | | | | | | | | | r1c13 | r1c14 |
|------|------|------|------|--|--|--|--|--|--|--|--|-------|-------|
| r2c1 | r2c2 | r2c3 | r2c4 | | | | | | | | | r2c13 | r2c14 |
| | | | | | | | | | | | | | |
| | | | | | | | | | | | | | |
| | | | | | | | | | | | | | |
| | | | | | | | | | | | | | |
| | | | | | | | | | | | | | |
| | | | | | | | | | | | | | |

FIG.4B

CHANNEL DIRECTION →

ROW DIRECTION ↓

| r1c1 | r1c2 | r1c3 | r1c4 | | | | | | | | | r1c13 | r1c14 |
|------|------|------|------|--|--|--|--|--|--|--|--|-------|-------|
| r2c1 | r2c2 | r2c3 | r2c4 | | | | | | | | | r2c13 | r2c14 |
| | | | | | | | | | | | | | |
| | | | | | | | | | | | | | |
| | | | | | | | | | | | | | |
| | | | | | | | | | | | | | |
| | | | | | | | | | | | | | |
| | | | | | | | | | | | | | |

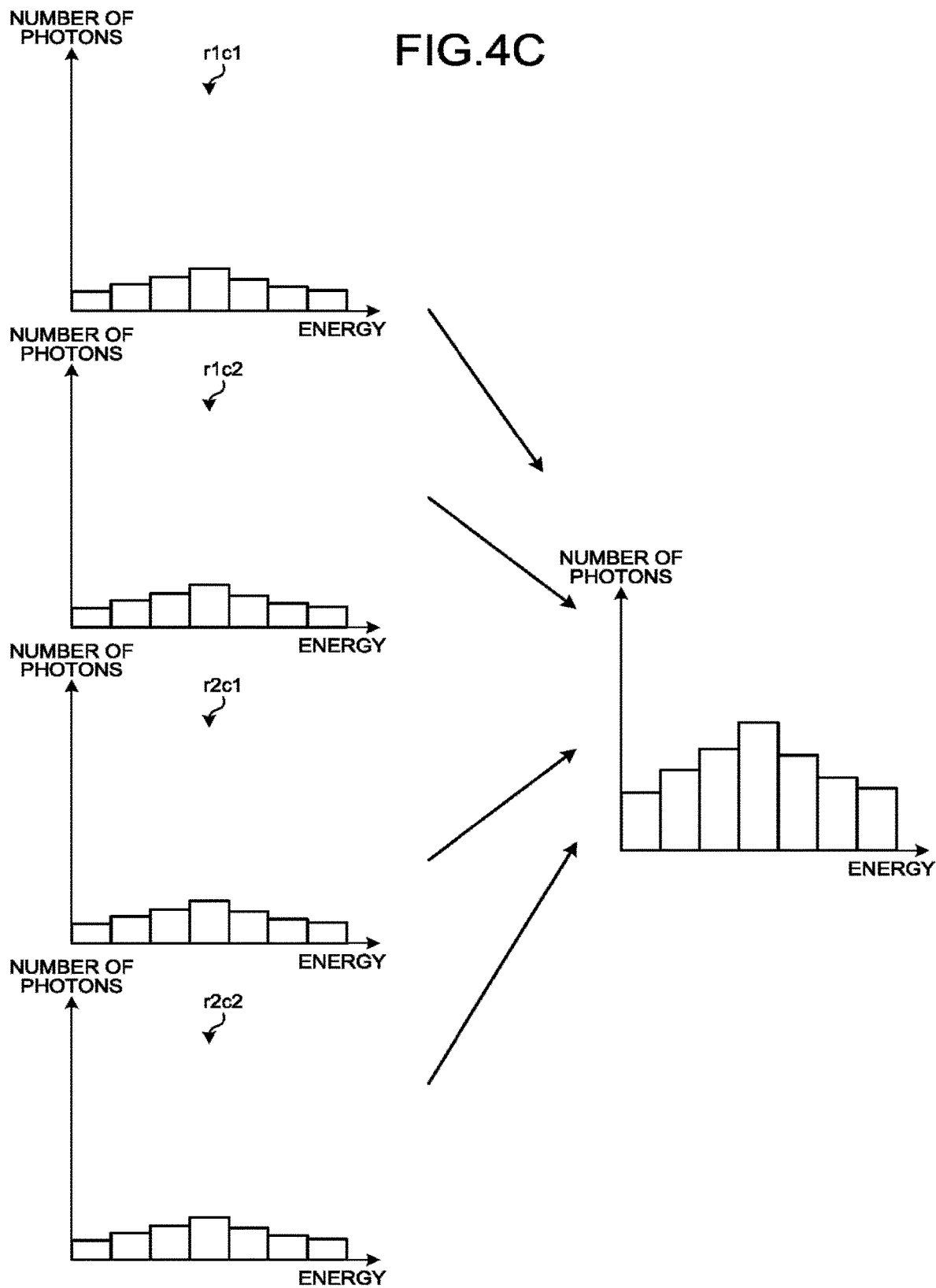

X-RAY CT APPARATUS

CROSS-REFERENCE TO RELATED APPLICATIONS

This application is based upon and claims the benefit of priority from Japanese Patent Application No. 2017-079701, filed on Apr. 13, 2017; and Japanese Patent Application No. 2018-075586, filed on Apr. 10, 2018; the entire contents of which are incorporated herein by reference.

FIELD

Embodiments described herein relate generally to an X-ray CT apparatus.

BACKGROUND

During a photon counting Computed Tomography (CT) process, energy levels of X-rays that have become incident are measured by counting individual incident X-rays so as to obtain a spectrum of X-rays that have passed through an examined subject. After that, in the photon counting CT process, materials contained in the examined subject are identified on the basis of the obtained spectrum so as to generate an image of the materials.

Further, it has become more and more necessary in recent years to reduce radiation exposure amounts during medical examinations. Because photon counting CT processes are not affected by circuit noise in contrast to conventional CT processes of integral types, photon counting CT processes are able to reconstruct images having high quality. For this reason, a photon counting CT process is expected to require a lower radiation dose to acquire an image having a similar level of image quality to that of an image acquired by performing a conventional integral-type CT process. As explained herein, also from the viewpoint of reducing radiation exposure amounts, there is a demand for making photon counting CT processes available in products available on market.

BRIEF DESCRIPTION OF THE DRAWINGS

FIG. 3 is a flowchart illustrating a processing procedure performed by the X-ray CT apparatus according to the first embodiment;

FIG. 4A is a drawing for explaining the first embodiment;

FIG. 4B is another drawing for explaining the first embodiment;

FIG. 4C is yet another drawing for explaining the first embodiment;

Figure 9:
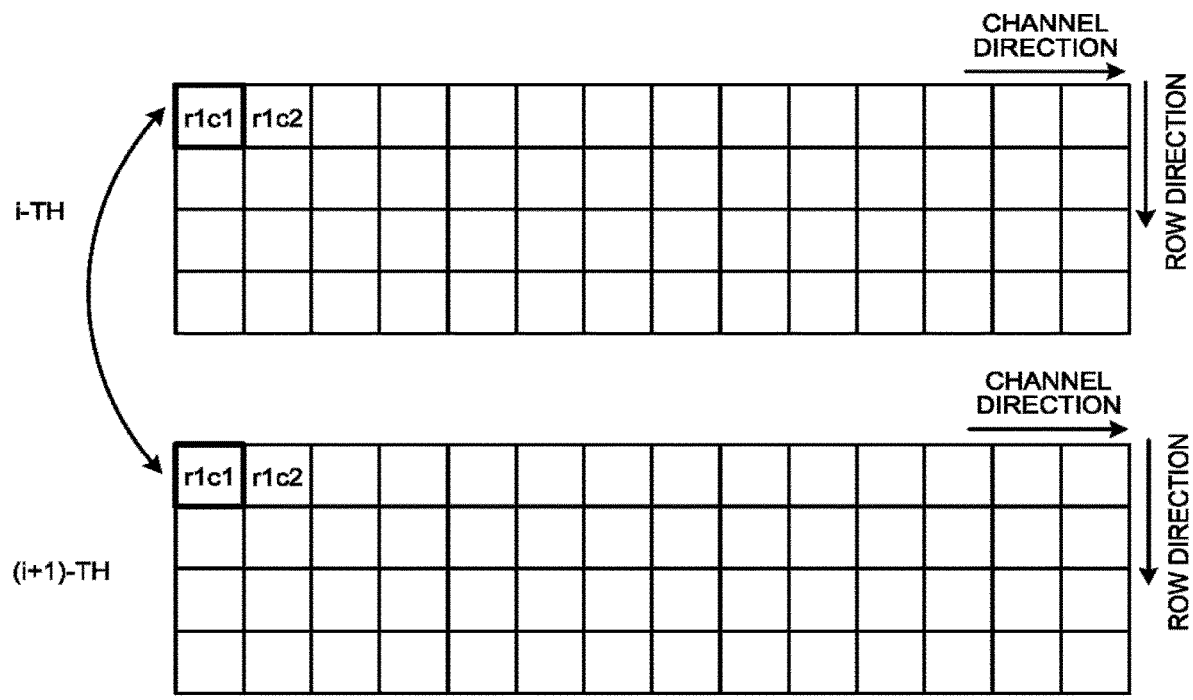
Figure 10:
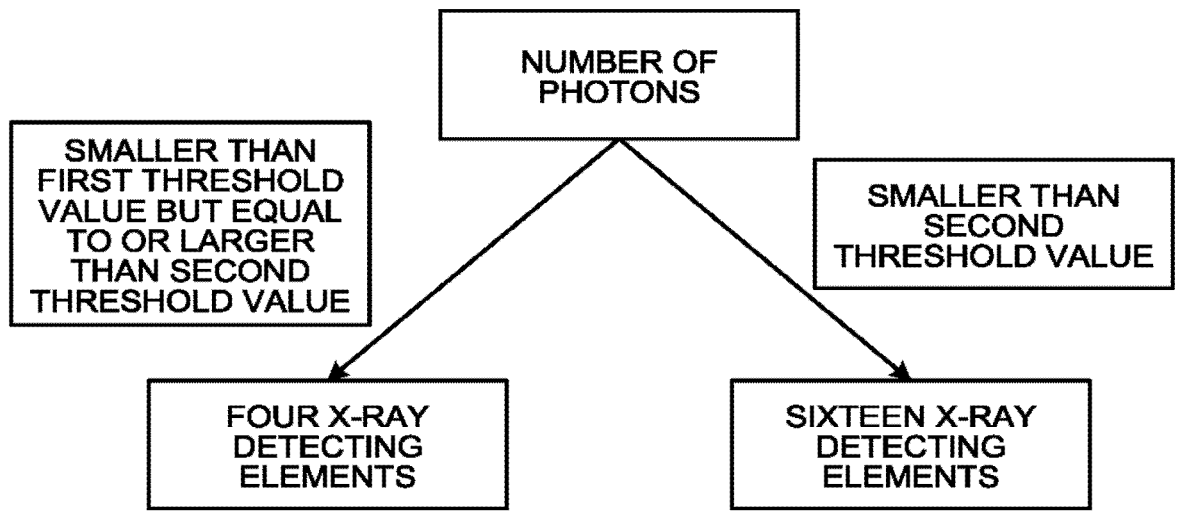
Figure 11:
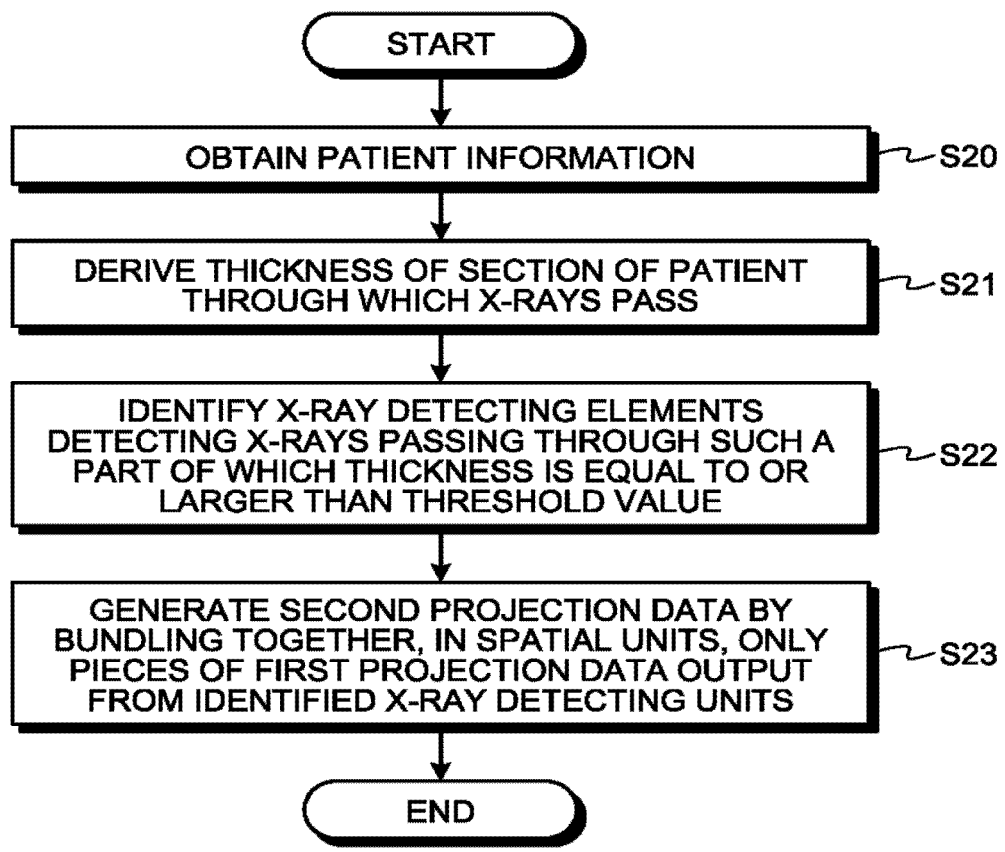

FIG. is a drawing for explaining a modification example of the first embodiment;

FIG. 9 is a drawing for explaining a second embodiment;

FIG. 10 is a drawing for explaining an example of a process performed when the number of photons is smaller than a second threshold value; and FIG. 11 is a flowchart illustrating an exemplary flow in a second projection data generating process according to a modification example.

DETAILED DESCRIPTION

An X-ray CT apparatus according to an embodiment includes a photon counting detector, and processing circuitry. The photon counting detector includes a plurality of detecting elements each of which outputs signals corresponding to numbers of photons that are counted. The processing circuitry generates pieces of first projection data on a basis of the signals from the plurality of detecting elements. The processing circuitry generate second projection data by bundling together, in spatial units, pieces of first projection data from a predetermined number of detecting elements among the plurality of detecting elements. The processing circuitry reconstructs a material decomposition image on a basis of the second projection data.

Exemplary embodiments of an X-ray CT apparatus will be explained, with reference to the accompanying drawings.

An example of the X-ray Computed Tomography (CT) apparatuses described in the embodiments below is an apparatus capable of performing a photon counting CT process. In other words, an example of the X-ray CT apparatuses described in the embodiments below is an apparatus capable of reconstructing X-ray CT image data having a high Signal-to-Noise (SN) ratio, by counting X-rays that have passed through a subject by using, not a conventional integral-type detector (using a current mode measuring scheme), but a detector based on a photon counting scheme. In principle, the description of each of the embodiments is similarly applicable to any other embodiments.

First Embodiment

Figure 1:
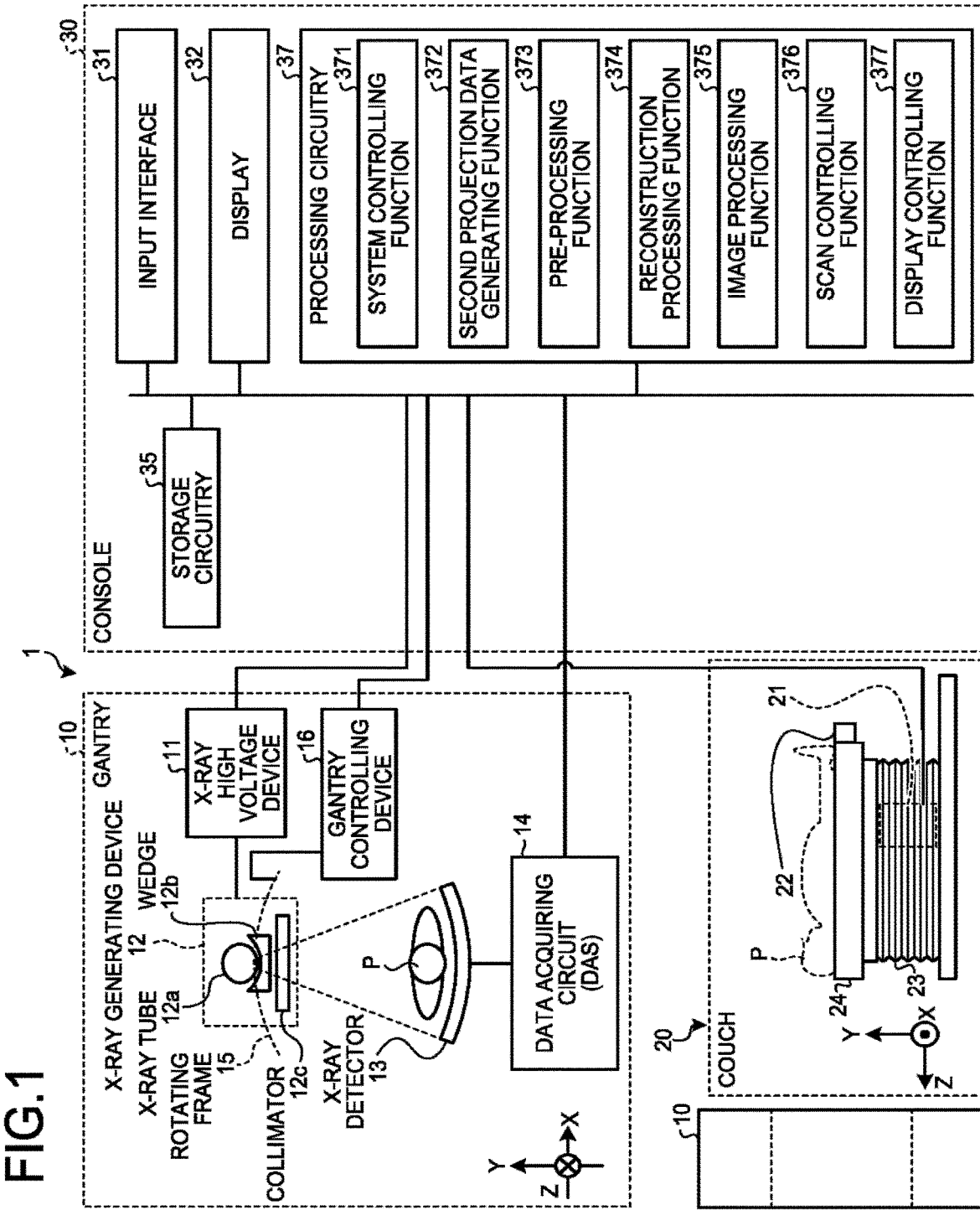
FIG. 1 is a diagram illustrating an exemplary configuration of an X-ray CT apparatus according to a first embodiment.

FIG. 1 is a diagram illustrating an exemplary configuration of an X-ray CT apparatus according to a first embodiment. As illustrated in FIG. 1, an X-ray CT apparatus 1 according to the first embodiment includes a gantry 10, a couch 20, and a console 30.

The gantry 10 is a device configured to radiate X-rays onto a subject P and to acquire data related to X-rays that have passed through the subject P. The gantry 10 includes an X-ray high voltage device 11, an X-ray generating device 12, an X-ray detector 13, a data acquiring circuit 14, a rotating frame 15, and a gantry controlling device 16. Further, as illustrated in FIG. 1, in the gantry 10, an orthogonal coordinate system structured with an X-axis, a Y-axis, and a Z-axis is defined. In other words, the X-axis expresses the horizontal direction, while the Y-axis expresses the vertical direction, and the Z-axis expresses the axial direction of the rotation center of the rotating frame 15 observed while the gantry 10 is not tilted.

The rotating frame 15 is an annular frame configured to support the X-ray generating device 12 and the X-ray detector 13 so as to oppose each other while the subject P is interposed therebetween and configured to be rotated by the gantry controlling device 16 (explained later) at a high speed on a circular orbit centered on the subject P.

The X-ray generating device 12 is a device configured to generate an X-ray and radiate the generated X-ray onto the subject P. The X-ray generating device 12 includes an X-ray tube 12*a*, a wedge 12*b*, and a collimator 12*c*.

The X-ray tube 12*a* is a vacuum tube configured to receive a supply of high voltage from the X-ray high voltage device 11 and to emit thermo electrons from a negative pole (which may be called a filament) to a positive pole (a target). As the rotating frame 15 rotates, the X-ray tube 12*a* radiates an X-ray beam onto the subject P. In other words, the X-ray tube 12*a* is configured to generate X-rays by using the high voltage supplied thereto from the X-ray high voltage device 11.

Further, the X-ray tube 12*a* is configured to generate an X-ray beam that spreads with a fan angle and a cone angle. For example, under the control of the X-ray high voltage device 11, the X-ray tube 12*a* is capable of continuously emitting X-rays in the entire surrounding of the subject P to realize a full reconstruction process and is capable of continuously emitting X-rays in an emission range (180 degrees+the fan angle) that enables a half reconstruction to realize a half reconstruction process. Further, under the control of the X-ray high voltage device 11, the X-ray tube 12*a* is capable of intermittently emitting X-rays (pulse X-rays) in positions (X-ray tube positions) set in advance. Further, the X-ray high voltage device 11 is also capable of modulating the intensities of the X-rays emitted from the X-ray tube 12*a*. For example, the X-ray high voltage device 11 increases the intensities of the X-rays emitted from the X-ray tube 12*a* in a specific X-ray tube position and decreases the intensities of the X-rays emitted from the X-ray tube 12*a* in a range other an the specific X-ray tube position.

The wedge 12*b* is an X-ray filter configured to adjust the X-ray dose of the X-rays emitted from the X-ray tube 12*a*. More specifically, the wedge 12*b* is a filter configured to pass and attenuate the X-rays emitted from the X-ray tube 12*a*, so that the X-rays radiated from the X-ray tube 12*a* onto the subject P have a predetermined distribution. For example, the wedge 12*b* is a filter obtained by processing aluminum so as to have a predetermined target angle and a predetermined thickness. The wedge may be referred to as a wedge filter or a bow-tie filter.

The collimator 12*c* is configured by using a lead plate or the like and has a slit in a part thereof. For example, by using the slit, the collimator 12*c* is configured to narrow down the radiation range of the X-rays of which the X-ray dose has been adjusted by the wedge 12*b*, under the control of the X-ray high voltage device 11 (explained later).

The source of the X-rays from the X-ray generating device 12 is not limited to the X-ray tube 12*a*. For example, in place of the X-ray tube 12*a*, the X-ray generating device 12 may be structured by using a focus coil configured to converge an electron beam generated from an electron gun, a deflection coil configured to electromagnetically deflect the electron beam, and a target ring positioned to cover a semi circumference of the subject P and configured to generate X-rays by having the deflected electron beam collide therewith.

The X-ray high voltage device 11 is structured by using an electric circuit including a transformer, a rectifier, and/or the like and is configured to include a high-voltage generating device having a function of generating the high voltage to be applied to the X-ray tube 12*a* and an X-ray controlling device that controls the output voltage in accordance with the X-rays radiated by the X-ray tube 12*a*. The high-voltage generating device may be of a transformer type or an inverter type. For example, the X-ray high voltage device 11 is configured to adjust the X-ray dose radiated on the subject P by adjusting the X-ray tube voltage and/or the X-ray tube current supplied to the X-ray tube 12*a*. Further, the X-ray high voltage device 11 is controlled by processing circuitry 37 included in the console 30.

The gantry controlling device 16 is structured by using processing circuitry configured with a Central Processing Unit (CPU) or the like and a driving mechanism configured with a motor, an actuator, and the like. The gantry controlling device 16 has a function of controlling operations of the gantry 10, by receiving an input signal from either an input interface 31 attached to the console 30 or an input interface attached to the gantry 10. For example, the gantry controlling device 16 is configured to exercise control so as to cause the X-ray tube 12*a* and the X-ray detector 13 to revolve on a circular orbit centered on the subject P, so as to tilt the gantry 10, or so as to bring the couch 20 and the couchtop 22 into operation, by turning the rotating frame 15 upon receipt of the input signal. The gantry controlling device 16 is controlled by the processing circuitry 37 included in the console 30.

The X-ray detector 13 is an example of a photon counting detector that includes a plurality of detecting elements and is configured to output signals corresponding to numbers of photons that are counted. For example, the X-ray detector 13 is structured with a plurality of rows of X-ray detecting elements (which may be referred to as "sensors" or simply "detecting elements") each of which includes a plurality of X-ray detecting elements arranged in a channel direction along one arc centered on a focal point of the X-ray tube 12*a*. The X-ray detector 13 has such as structure that has such a structure that the plurality of rows of X-ray detecting elements are arranged in a slice direction, while each row of X-ray detecting elements includes the plurality of X-ray detecting elements that are arranged in the channel direction. Each of the X-ray detecting elements included in the X-ray detector 13 is configured to detect X-rays that were emitted from the X-ray generating device 12 and have passed through the subject P and to output an electrical signal (a pulse) corresponding to the X-ray dose to the data acquiring circuit 14. The peak value of the electrical signal (the pulse) is correlated with the energy value of X-ray photons. The electrical signals output by the X-ray detecting elements may be referred to as detection signals.

Further, for example, the X-ray detector 13 is a detector of a direct conversion type structured by using a grid and a semiconductor element array configured to convert X-rays that have become incident thereto into electrical signals. The semiconductor element array may be structured with a plurality of compound semiconductors of cadmium zinc telluride (CdZnTe), cadmium telluride (CdTe), or the like or with an element semiconductor of silicon or the like and is configured to output the electrical signals corresponding to the X-ray dose that has become incident thereto. The grid is disposed on the surface of the semiconductor element array positioned on the X-ray incident side and is structured with an X-ray blocking plate having a function of absorbing scattered X-rays. Alternatively, the X-ray detector 13 may be a detector of an indirect conversion type structured by using a grid, a scintillator array, and an optical sensor array. The scintillator array is structured with a plurality of scintillators each of which is structured with a scintillator crystal that outputs light having a photon quantity corresponding to the X-ray dose that has become incident thereto. The grid is disposed on the surface of the scintillator array positioned on the X-ray incident side and is structured with an X-ray blocking plate having a function of absorbing scattered X-rays. The optical sensor array has a function of converting the light into electrical signals corresponding to the amounts of light output from the scintillators and may be structured with optical sensors such as photomultipliers, for example. In this situation, the optical sensors are silicon photomultipliers (SiSMs).

Figure 2A:
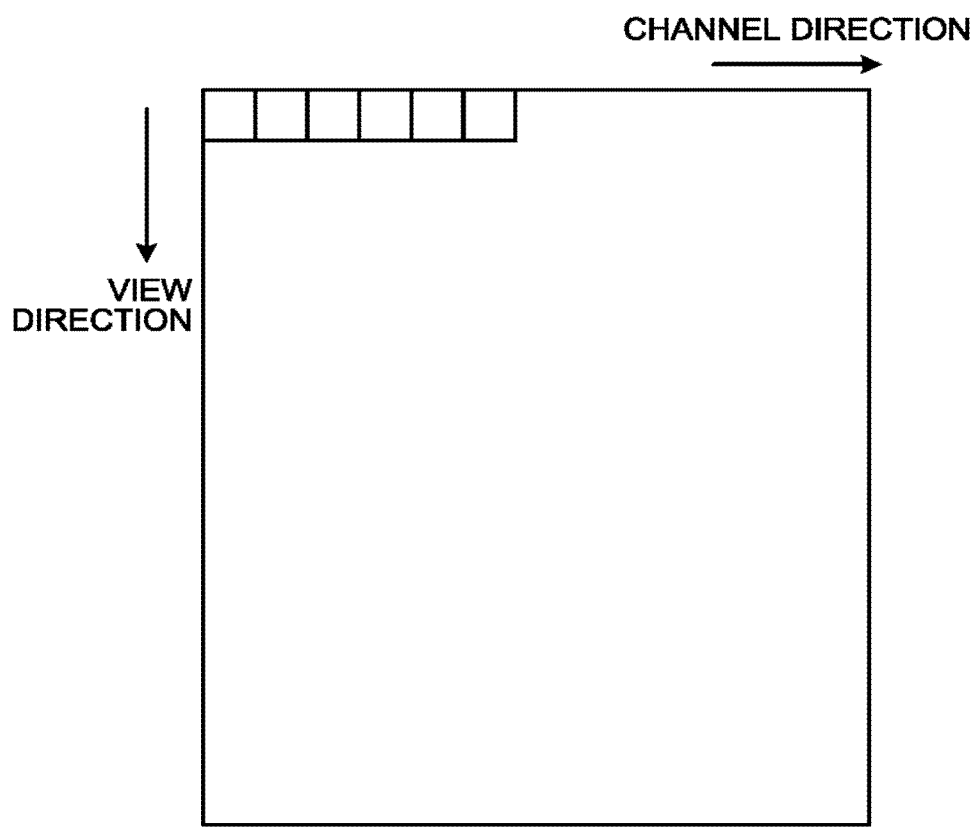
FIG. 2A is a drawing for explaining a sinogram according to the first embodiment.
Figure 2B:
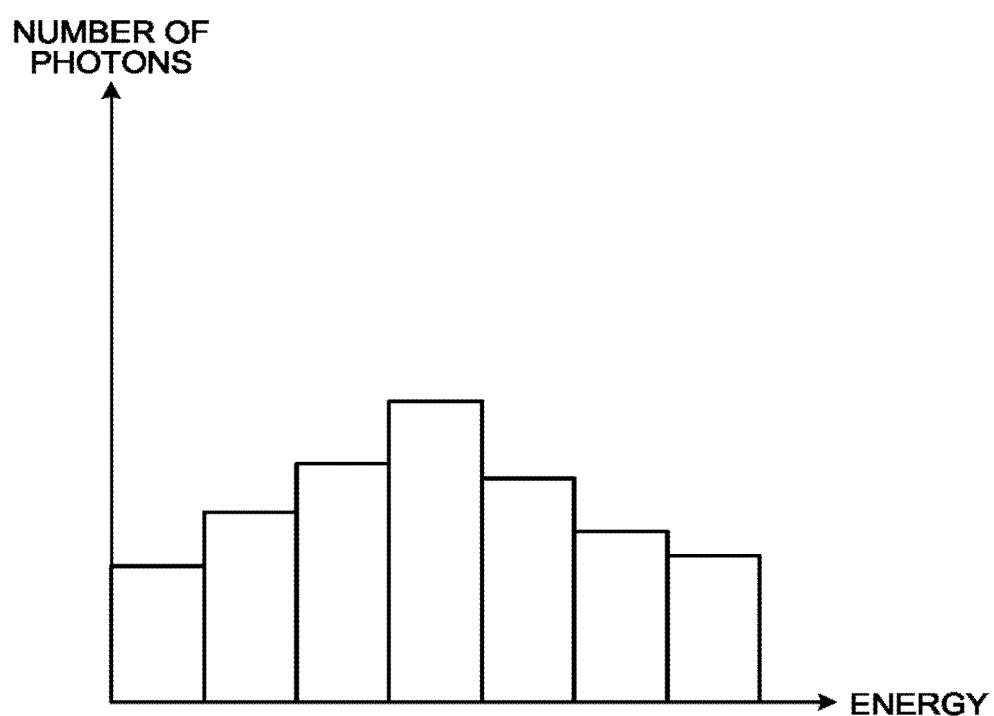
FIG. 2B is another drawing for explaining the sinogram according to the first embodiment.

The data acquiring circuit 14 (a Data Acquisition System [DAS]) is structured by using at least an amplifier configured to perform an amplifying process on the electrical signals output from the X-ray detecting elements included in the X-ray detector 13 and an Analog-to-Digital (A/D) converter configured to convert the electricals signals into digital signals. The data acquiring circuit 14 is configured to generate detection data, which is a result of a counting process performed by using the detection signals obtained by the X-ray detector 13. In this situation, the detection data may be represented by a sinogram, for example. The sinogram is data in which results of the counting process are arranged side by side, the results indicating the counts of incidences to the detecting elements in different positions of the X-ray tube 12a. FIGS. 2A and 2B are drawings for explaining the sinogram according to the first embodiment.

FIG. 2A illustrates an example of the sinogram. As illustrated in FIG. 2A, the sinogram is data in which the results of the counting process are arranged in a two-dimensional orthogonal coordinate system which the axes correspond to a view direction and the channel direction. For example, the data acquiring circuit 14 generates the sinogram in units of rows arranged in the slice direction within the X-ray detector 13.

FIG. 2B illustrates an example of the results of the counting process. As illustrated in FIG. 2B, the results of the counting process are represented by data in which the number of photons in the X-rays is assigned to each energy bin. For example, the data acquiring circuit 14 obtains the results of the counting process by counting the photons (the X-ray photons) derived from the X-rays that were emitted from the X-ray tube 12a and have passed through the subject P and further discriminating energy levels of the counted photons. In the example illustrated in FIG. 2B, the energy levels are divided into seven bins, so as to indicate the number of photons in each of the energy bins. In this situation, the number of energy bins into which the energy levels are divided does not necessarily have to be seven and may be set to an arbitrary value. The data acquiring circuit 14 is configured to transfer the generated detection data to the console 30. Further, the data acquiring circuit 14 is an example of the first generating unit.

The data output from the data acquiring circuit 14 will be referred to as detection data. In contrast, the data obtained by applying pre-processing processes such as a logarithmic transformation process, an offset correcting process, a sensitivity correcting process between the channels, a gain correcting process between the channels, a pile-up correcting process, a beam hardening correcting process, and/or the like, to the detection data will be referred to as raw data. Further, the detection data and the raw data will collectively be referred to as projection data.

The couch 20 is a device on which the subject P subject to a scan is placed and is configured to move the subject P. The couch 20 includes a couch driving device 21, a couchtop 22, a pedestal 23, and a base (a supporting frame) 24.

The couchtop 22 is a board on which the subject P is placed. The base 24 is configured to support the couchtop 22. The pedestal 23 is a casing member configured to support the base 24 in such a manner that the base 24 is movable in the vertical direction. The couch driving device 21 is a motor or an actuator configured to move the couchtop 22 on which the subject P is placed in the longitudinal direction of the couchtop 22 so as to move the subject P into the rotating frame 15. The couch driving device 21 is also capable of moving the couchtop 22 in the X-axis direction.

As for the method for moving the couchtop 22, only the couchtop 22 may be moved, or the couch 20 may be moved together with the base 24. Further, when a standing CT process is performed, another method may be used by which a subject moving mechanism corresponding to the couchtop 22 is moved.

For example, the gantry 10 performs a helical scan by which the subject P is helically scanned by causing the rotating frame 15 to rotate while the couchtop 22 is being moved. In another example, the gantry 10 performs a conventional scan by which the subject P is scanned on a circular orbit by causing the rotating frame 15 to rotate, while the position of the subject P is being fixed after the couchtop 22 is moved. In the embodiments described below, an example will be explained in which the relative position between the gantry 10 and the couchtop 22 can be changed by controlling the couchtop 22; however, possible embodiments are not limited to this example. For instance, when the gantry 10 is self-propelled, the relative position between the gantry 10 and the couchtop 22 may be changed by controlling the self-propelled movement of the gantry 10. Alternatively, the relative position between the gantry 10 and the couchtop 22 may be changed by controlling the movement of the gantry 10 and the couchtop 22.

The console 30 is a device configured to receive operations performed by the operator on the X-ray CT apparatus 1 and also configured to reconstruct X-ray CT image data by using the count results acquired by the gantry 10. As illustrated in FIG. 1, the console 30 includes the input interface 31, a display 32, storage circuitry 35, and the processing circuitry 37.

The input interface 31 is configured to receive various types of input operations from the operator, to convert the received input operations into electrical signals, and to output the electrical signals to the processing circuitry 37. For example, the input interface 31 is configured to receive, from the operator, an acquisition condition used when the projection data is acquired, a reconstruction condition used when a CT image is reconstructed, an image processing condition used when a post-processing image is generated froze a CT image, and/or the like. For example, the input interface 31 is realized with a mouse, a keyboard, a track ball, a switch, a button, a joystick, and/or the like. Further, the input interface 31 is an example of an input unit.

The display 32 is configured to display various types of information. For instance, the display 32 is configured to output a medical image (a CT image) generated by the processing circuitry 37, a Graphical User interface (GUI) used for receiving various types of operations from the operator, and the like. For example, the display 2 is configured by using a liquid crystal display, a Cathode Ray Tube (CRT) display, or the like.

For example, the storage circuitry 35 is realized with a semiconductor memory such as a Random Access Memory (RAM) or a flash memory, a hard disk, an optical disk, or the like. For example, the storage circuitry 35 is configured to store therein the projection data and reconstructed image data.

For example, the processing circuitry 37 executes a system controlling function 371, a second projection data generating function 372, a pre-processing function 373, a reconstruction processing function 374, an image processing function 375, a scan controlling function 376, and a display controlling function 377. In this situation, for example, the processing functions executed by the constituent elements of the processing circuitry 37 illustrated in FIG. 1, namely, the system controlling function 371, the second projection data generating function 372, the pre-processing function 373, the reconstruction processing function 374, the image processing function 375, the scan controlling function 6, and the display controlling function 377, are recorded in the storage circuitry 35 in the form of computer-executable programs. The processing circuitry 37 may be a processor, for example, and is configured to read and execute the programs from the storage circuitry 35 so as to realize the functions corresponding to the read programs. In other words, the processing circuitry 37 that has read the programs has the functions illustrated within the processing circuitry 37 in FIG. 1.

The system controlling function 371 is configured to control the various types of functions of the processing circuitry 37, on the basis of input operations received from the operator via the input interface 31.

The second projection data generating function 372 is configured to generate detection data obtained by bundling together, in spatial units, pieces of detection data from a predetermined number of detecting elements. In the following sections, for the sake of convenience in the explanation, the detection data generated by the data acquiring circuit 14 will be referred to as "first projection data", whereas the detection data bundled together in the spatial units by the second projection data generating function 372 will be referred to as "second projection data". Details of the second projection data generating function 372 will be explained later. Further, the second projection data generating function 372 is an example of the second generating unit.

The pre-processing function 373 is configured to generate the raw data by performing a pre-processing process such as a logarithmic transformation process, an offset correcting process, a sensitivity correcting process between the channels, a gain correcting process between the channels, a pile-up correcting process, a beam hardening correcting process, and/or the like, on the detection data (the first projection data) output from the data acquiring circuit 14. Further, the pre-processing function 373 is configured to generate the raw data by performing a pre-processing process such as a logarithmic transformation process, an offset correcting process, a sensitivity correcting process between the channels, a gain correcting process between the channels, a pile-up correcting process, a beam hardening correcting process, and/or the like, on the second projection data generated by the second projection data generating function 372. The raw data generated by performing the pre-processing process on the first projection data will be referred to as first raw data, whereas the raw data generated by performing the pre-processing process on the second projection data will be referred to as second raw data.

The reconstruction processing function 374 is configured to generate CT image data by performing a reconstruction process that uses a filter correction back projection method or a successive approximation reconstruction method, on the projection data generated by the pre-processing function 373. The reconstruction processing function 374 is configured to store the reconstructed CT image data into the storage circuitry 35. In this situation, CT image data reconstructed from data including total energy information by adding together pieces of information of all the bins in units of pixels may be referred to as a "base image".

In this situation, the projection data generated from the count results obtained from a photon counting CT process includes information about energy of the X-rays that were attenuated as a result of passing through the subject P. For this reason, for example, the reconstruction processing function 374 is able to reconstruct X-ray CT image data corresponding to a specific energy component. Further, the reconstruction processing function 374 is able to reconstruct X-ray CT image data corresponding to each of a plurality of energy components, for example.

Further, the reconstruction processing function 374 is configured to assign a color tone corresponding to an energy component to each of the pixels in each of a plurality of pieces of X-ray CT image data corresponding to the energy components and to generate image data in which the plurality of pieces of X-ray CT image data that are color-coded in accordance with the energy components are superimposed on one another. Further, for example, the reconstruction processing function 374 is capable of generating image data with which it is possible to identify materials by using the k-absorption edge unique to each material. Other examples of image data generated by the reconstruction processing function 374 include monochrome X-ray image data, density image data, and effective atomic number image data, and the like.

Further, as an application of X-ray CT, a technique is known by which types, content amounts, density levels, and the like of materials contained in an examined subject are discriminated, by using the fact that X-ray absorption characteristics are different among different materials. This technique is called material decomposition. For example, the reconstruction processing function 374 is configured to perform a material decomposition process on the projection data and to obtain material decomposition information. Further, the reconstruction processing function 374 is configured to reconstruct a material decomposition image by using the material decomposition information resulting from the material decomposition process.

To reconstruct a CT image, the reconstruction processing function 374 is able to use a full-scan reconstruction scheme and a half-scan reconstruction scheme. For example, when using the full-scan reconstruction scheme, the reconstruction processing function 374 requires projection data from the entire surrounding of the subject corresponding to 360 degrees. In contrast, when using the half-scan reconstruction scheme, the reconstruction processing function 374 requires projection data corresponding to 180 degrees+a fan angle. In the following sections, to keep the explanation simple, it is assumed that the reconstruction processing function 374 uses the full-scan reconstruction scheme by which the reconstruction process is performed by using projection data from the entire surrounding of the subject corresponding to 360 degrees.

The image processing function 375 is configured to convert the CT image data generated by the reconstruction processing function 374 into image data of a tomographic image on an arbitrary cross-sectional plane or a three-dimensional image resulting from a rendering process, by using any of publicly-known methods, on the basis of input operations received from the operator via the input interface 31. The image processing function 375 is configured to store the image data resulting from the conversion into the storage circuitry 35.

The scan controlling function 376 is configured to control the CT scan performed by the gantry 10. For example, the scan controlling function 376 controls the start of the scan, the execution of the scan, and the end of the scan performed by the gantry 10, by controlling operations of the X-ray high voltage device 11, the X-ray detector 13, the gantry controlling device 16, the data acquiring circuit 14, and the couch driving device 21. More specifically, the scan controlling function 376 controls projection data acquiring processes during an image taking process to acquire a position determining image (a scanogram image) and during a main image taking process (a scan) to acquire one or more images used for diagnosis purposes.

The display controlling function 377 is configured to exercise control so that the display 32 displays any of the various types of image data stored in the storage circuitry 35.

An exemplary configuration of the X-ray CT apparatus 1 according to the first embodiment has thus been explained. The X-ray CT apparatus 1 according to the first embodiment configured as described above is configured to perform the material decomposition process on the projection data and to reconstruct the material decomposition image by using the result of the material decomposition process. Incidentally, to perform the material decomposition process, it is necessary to detect small differences in spectra with a high level of precision. For this reason, the image taking process requires a higher X-ray dose when the material decomposition process is performed than when a base image generating process is performed. However, to perform the material decomposition process, when the image taking process is performed with a higher X-ray dose than when the base image generating process is performed, the radiation exposure amount for the subject increases. Because such an increase in the radiation exposure amount for the subject is clinically not acceptable, it is not necessarily desirable in the actual clinical environment to perform image taking processes with higher X-ray doses for the material decomposition purposes. As a result, image taking processes for material decomposition purposes tend to be performed with the same X-ray dose as used for base image generating processes. Accordingly, a problem arises where the precision level of material decomposition processes remains low.

To cope with this situation, the X-ray CT apparatus 1 according to the first embodiment performs a material decomposition process described below for the purpose of realizing a high material decomposition capability. In other words, the X-ray CT apparatus 1 is configured to generate the second projection data by bundling together, in spatial units, pieces of first projection data from a predetermined number of detecting elements. Further, the X-ray CT apparatus 1 is configured to reconstruct a material decomposition image on the basis of the second projection data.

FIG. 3 is a flowchart illustrating a processing procedure performed by the X-ray CT apparatus 1 according to the first embodiment. While FIG. 3 presents the flowchart for explaining operations performed by the X-ray CT apparatus 1, the steps in the flowchart to which each of the constituent elements corresponds will be explained.

Step S1 is a step corresponding to the scan controlling function 376. Step S1 is a step at which the scan controlling function 376 is realized as a result of the processing circuitry 37 invoking and executing a predetermined program corresponding to the scan controlling function 376 from the storage circuitry 35. At step S1, the scan controlling function 376 performs a scan.

Step S2 is a step realized by the data acquiring circuit 14. At step the data acquiring circuit. 14 generates the first projection data. For example, as the first projection data, the data acquiring circuit 14 generates the detection data represented by the results f the counting process performed by using the detection signals from the X-ray detector 13. In other words, the data acquiring circuit 14 generates the first projection data on the basis of the signals from the plurality of detecting elements.

Step S3 is a step corresponding to the reconstruction processing function 374. Step S3 is a step at which the reconstruction processing function 374 is realized as a result of the processing circuitry 37 invoking and executing a predetermined program corresponding to the reconstruction processing function 374 from the storage circuitry 35. At step 33, the reconstruction processing function 374 reconstructs a base image. For example, the reconstruction processing function 374 generates the base image on the basis of the first projection data.

Step S4 is a step corresponding to the display controlling function 377. Step S4 is a step at which the display controlling function 377 is realized as a result of the processing circuitry 37 invoking and executing a predetermined program corresponding to the display controlling function 377 from the storage circuitry 35. At step S4, the display controlling function 377 displays the base image on the display 32.

Steps S5 and S6 are steps started in the background of steps S3 and S4, in conjunction with the process at step S3 being started. Step S5 is a step corresponding to the second projection data generating function 372. Step S5 is a step at which the second projection data generating function 372 is realized as a result of the processing circuitry 37 invoking and executing a predetermined program corresponding to the second projection data generating function 372 from the storage circuitry 35. At step S5, the second projection data generating function 372 generates the second projection data. In this situation, the second projection data generating function 372 starts the second projection data generating process as being triggered by the start of the base image reconstruction process performed by the reconstruction processing function 374. Alternatively, the second projection data generating function 372 may start the second projection data generating process as being triggered by receiving the first projection data from the data acquiring circuit 14. After that, for example, the second projection data generating function 372 generates the second projection data by bundling together, in spatial units, the pieces of first projection data from the predetermined number of detecting elements.

FIGS. 4A, 4B, and 4C are drawings for explaining the first embodiment. FIGS. 4A and 4B illustrate a part of the detecting elements included in the X-ray detector 13. Further, FIGS. 4A and 4B each illustrate the channel direction and the row direction. In the present example, for the sake of convenience in the explanation, FIGS. 4A and 4B each illustrate a group of 14×8 detecting elements, with fourteen detecting elements arranged in the channel direction and eight detecting elements arranged in the row direction. However, the array pattern of the detecting elements in the channel direction and the row direction in the group of detecting elements according to possible embodiments are not limited to the one in this example and may arbitrarily be changed.

For example, the second projection data generating function 372 is configured to add together pieces of first projection data from a plurality of detecting elements that are positioned adjacent to each other in the channel direction and the row direction in the photon counting detector, as the bundling in the spatial units.

In one example, in the group of 14×6 detecting elements illustrated in FIG. 4A, the second projection data generating function 372 organizes groups each made up of four detecting elements corresponding to 2×2 pixels, as illustrated in FIG. 4B. In other words, the second projection data generating function 372 bundles together the 14×6 detecting elements into the spatial units, so as to form seven groups arranged in the channel direction and four groups arranged in the row direction.

More specifically, the second projection data generating function 372 bundles together detecting elements r1c1, r1c2, r2c1, and r2c2 illustrated in FIG. 4A into one group. Further, the second projection data generating function 372 similarly bundles together detecting elements r1c3, r1c4, r2c3, and r2c4 illustrated in FIG. 4A into another group.

After that, the second projection data generating function 372 adds together the pieces of first projection data in each of the bundled groups. For example, the second projection data generating function 372 adds together the pieces of first projection data from the detecting elements r1c1, r1c2, r2c1, and r2c2 illustrated in FIG. 4A. In other words, the second projection data generating function 372 adds together the numbers of photons in the X-rays in each of the energy bins with respect to the piece of first projection data from the detecting element r1c1, the piece of first projection data from the detecting element r1c2, the piece of first projection data from the detecting element r2c1, and the piece of first projection data from the detecting element r2c2. The process of adding together the numbers of photons in the X-rays in each of the energy bins with respect to the pieces of first projection data will be explained, with reference to FIG. 4C.

Illustrated in the left section of FIG. 4C are the piece of first projection data from the detecting element r1c1, the piece of first projection data from the detecting element r1c2, the piece of first projection data from the detecting element r2c1, and the piece of first projection data from the detecting element r2c2, from the top to the bottom of the drawing in the stated order. In FIG. 4C, each of the pieces of first projection data indicates the number of photons in each of the seven energy bins. The second projection data generating function 372 generates the second projection data illustrated in the right section of FIG. 4C, by adding together the numbers of photons in the X-rays for each of the energy bins, with respect to the pieces of first projection data.

More specifically, in the first projection data, let us assume that the energy bins are sequentially referred to as E1 to E7 ranging from the lowest energy level to the energy level. The numbers of photons from the detecting elements in each of the energy bins are added together. For example, the second projection data generating function 372 simply adds together the number of photons from the detecting element r1c1, the number of photons from the detecting element r1c2, the number of photons from the detecting element r2c1, and the number of photons from the detecting element r2c2, each in the energy bin E1. By similarly adding together the numbers of photons for each of the energy bins E2 to E7, the second projection data generating function 372 generates the second projection data illustrated in the right section of FIG. 4C. As illustrated in the right section of FIG. 4C, the second projection data has a larger number of photons in each of the energy bins, compared to the number of photons in each of the energy bins in each of the pieces of first projection data. As a result, the second projection data has a larger statistic amount. In other words, the second projection data generating function 372 increases the statistic amount by sacrificing the spatial resolution (the degree of resolution). Further, when it is desired to further improve the level of precision in the material decomposition process even though the degree of resolution is sacrificed, the second projection data generating function 372 may increase the statistic amount by organizing groups each made up of sixteen detecting elements corresponding to 4×4 pixels, for example.

Returning to the description of FIG. 3, step 36 is a step corresponding to the reconstruction processing function 374. Step 36 is a step at which the reconstruction processing function 374 is realized as a result of the processing circuitry 37 invoking and executing a predetermined program corresponding to the reconstruction processing function 374 from the storage circuitry 3o. At step S6, the reconstruction processing function 374 reconstructs a material decomposition image on the basis of the second projection data. For example, the reconstruction processing function 374 performs a material decomposition process on the second projection data and reconstructs a material decomposition image (a first material decomposition image) by using a result of the material decomposition process. In the following sections, for the sake of convenience in the explanation, an example will be explained in which the reconstruction processing function 374 identifies water, calcium, and iodine in the material decomposition process.

In this situation, the reconstruction processing function 374 may regard the material decomposition image reconstructed by using the result from the material decomposition process performed on the second projection data, as a final material decomposition image. However, because the second projection data is obtained by bundling together the pieces of first projection data, the spatial resolution is degraded. For this reason, the material decomposition information obtained as a result the material decomposition process performed on the second projection data is material decomposition information having a low resolution. Accordingly, the reconstruction processing function 374 may generate a final material decomposition image (a second material decomposition image) by combining a base image having a higher resolution with the material decomposition image (the abovementioned first material decomposition image) reconstructed from the material decomposition information having the lower resolution. In other words, the reconstruction processing function 374 may be configured to further generate the base image on the basis of the pieces of first projection data, to generate images respectively corresponding to the energy bins and having a higher spatial resolution than the images that are based on the second projection data and respectively correspond to the plurality of energy bins, by using the base image and the images that are based on the second projection data and respectively correspond to the plurality of energy bins, and to reconstruct the second material decomposition image by using a result of a material decomposition process performed on the generated images corresponding to the energy bins. The second material decomposition image has a higher spatial resolution than that of the first material decomposition image described above. In this situation, for example, the reconstruction processing function 374 may use the hybrid reconstruction scheme disclosed in Japanese Patent Application Laid-open No. 2015-33581.

More specifically, the reconstruction processing function 374 reconstructs the first material decomposition image corresponding to each of the energy bins, from the material decomposition information having a lower resolution. After that, the reconstruction processing function 374 generates the final second material decomposition image by minimizing an objective functional between the first material decomposition images corresponding to the energy bins and the base image having a higher resolution.

In an example in which the number of pixels in the base image is 1024×1024, and the pieces of first projection data are bundled together in units of 2×2 pixels, the number of pixels in the material decomposition image will be 512×512

Accordingly, the number of pixels in the material decomposition image is smaller than the number of pixels in the base image. For this reason, when the second projection data is returned to image information, it is acceptable to arrange the number of pixels in the material decomposition image to be equal to the number of pixels in the base image, by returning the second projection data to the image information with a constant value for the bundled pixels on the basis of the number of photons added together. However, it should be noted that, even when the second projection data is returned to the image information by using the constant value for the bundled pixels, the spatial resolution of the material decomposition image will be lower than that of the base image.

Figure 5:
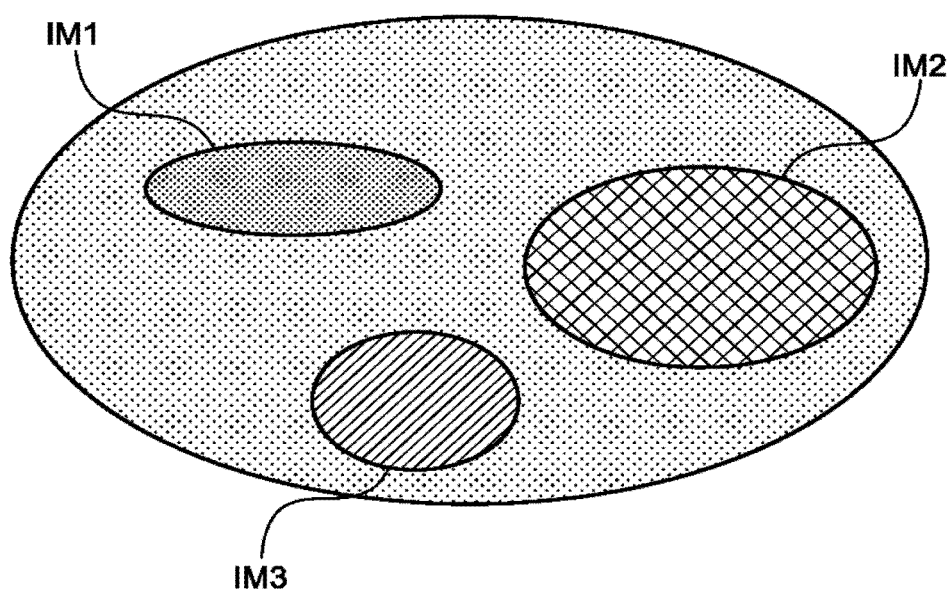
FIG. 5 is yet another drawing for explaining the first embodiment.

FIG. 5 is yet another drawing for explaining the first embodiment. FIG. 5 illustrates an example of a material decomposition image in which three types of materials such as material A (water), material B (calcium), and material C (iodine) are identified. As illustrated in FIG. 5, the reconstruction processing function 374 generates the material decomposition image in which mutually-different color tones are assigned to material A (IM1), material B (IM2), and material C (IM3).

Returning to the description of FIG. 3, step S7 is a step corresponding to the display controlling function 377. Step S7 is a step at which the display controlling function 377 is realized as a result of the processing circuitry 37 invoking and executing a predetermined program corresponding to the display controlling function 377 from the storage circuitry 35. At step S7, the display controlling function 377 displays the material decomposition image generated at step S6 on the display 32.

Figure 6:
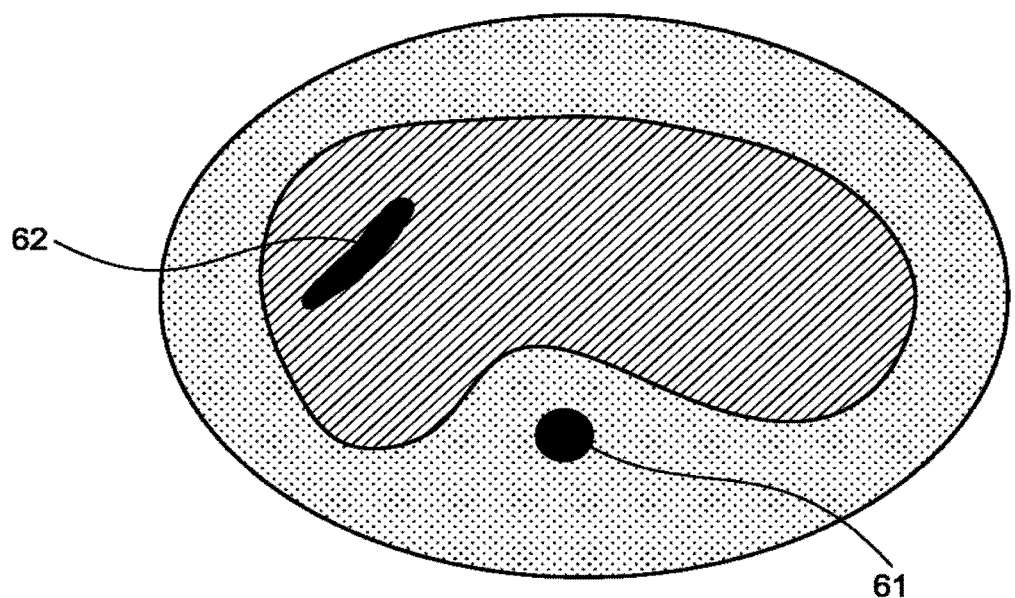
FIG. 6 is a drawing for explaining a comparison example.
Figure 7:
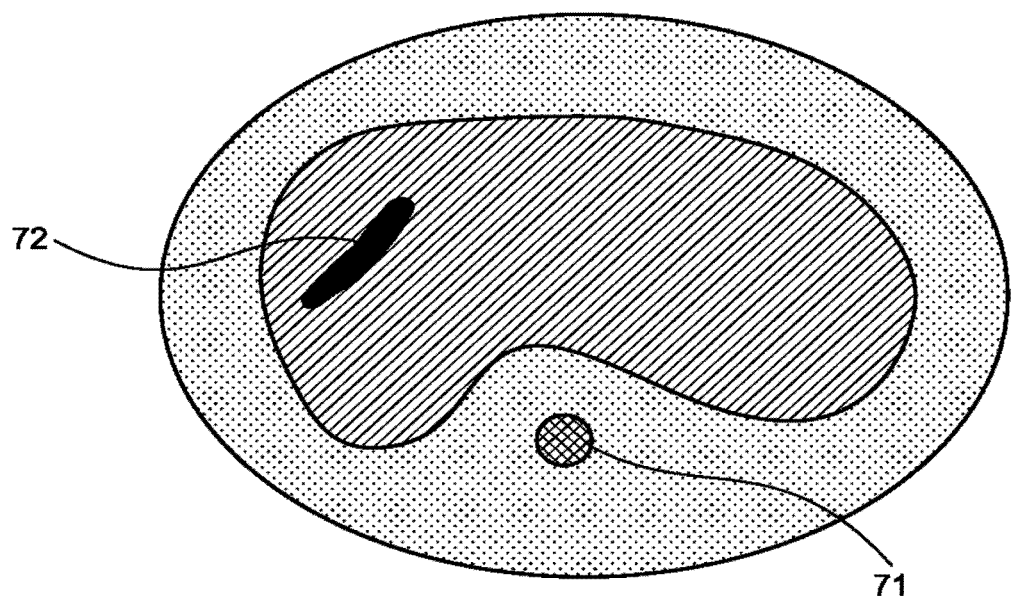
FIG. 7 is yet another drawing for explaining the first embodiment.

As explained above, in the first embodiment, the X-ray CT apparatus 1 is configured to generate the second projection data by bundling together, in the spatial units, the pieces of first projection data from the predetermined number of detecting elements and to reconstruct the material decomposition image on the basis of the second projection data. In this situation, the second projection data has a larger statistic amount than the statistic amounts of the pieces of first projection data because the second projection data is obtained by bundling together the pieces of first projection data in the spatial units. Accordingly, in the first embodiment, it is possible to realize a high material decomposition capability by using the second projection data that has a larger statistic amount than the statistic amounts of the pieces of first projection data. Next, an advantageous effect of the first embodiment will be explained, by using a comparison example in which a material decomposition image is generated without bundling the pieces of first projection data together in spatial units. FIG. 6 is a drawing for explaining the comparison example. FIG. 7 is a drawing for explaining the first embodiment.

FIG. 6 illustrates an example of a material decomposition image in the comparison example. FIG. 7 illustrates an example of a material decomposition image according to the first embodiment. FIGS. 6 and 7 each illustrate a material decomposition image in which a bone (calcium) and a blood vessel (iodine) rendered by a contrast agent are expressed in the image, as a result of a material decomposition process performed on calcium and iodine. In the comparison example, pieces of first projection data from the detecting elements are used. Because the statistic amounts of the numbers of photons corresponding to the energy bins are small, the level of precision of the material decomposition process is lower. Accordingly, in the comparison example, it is not possible to accurately discriminate the materials between calcium and iodine. As a result, in the comparison example, as illustrated in FIG. 6, for example, the material decomposition image is generated in which mutually the same color tone is assigned to a bone 61 and to a blood vessel 62.

In contrast, in the example illustrated in FIG. 7, the second projection data is generated by bundling together, in the spatial units, pieces of first projection data from a predetermined number of detecting elements. Accordingly, because the statistic amounts of the numbers of photons corresponding to the energy bins are larger, the level of precision of the material decomposition process is improved. For this reason, in the first embodiment, it is possible to accurately discriminate the materials between calcium and iodine. As a result, in the first embodiment, as illustrated in FIG. 7 for example, the material decomposition image is generated in which mutually-different color tones are assigned to a bone 71 and to a blood vessel 72.

In the embodiment described above, the example is explained in which the reconstruction processing function 374 identifies (discriminates) the materials among water, calcium, and iodine; however, possible embodiments are not limited to this example. For instance, the reconstruction processing function 374 may further perform a material decomposition process on one or more materials other than water, calcium, and iodine or may perform a material decomposition process on a set of materials made up of two or more selected from among water, calcium, and iodine. Further, the reconstruction processing function 374 may receive, from the operator, a selection of materials to be identified, via the input interface 31. In that situation, for example, when the base image is displayed on the display 32 at step S4 in FIG. 3, the selection of materials to be identified is received from the operator, by further displaying a list of identifiable materials.

Modification Examples of the First Embodiment

In the embodiment described above, the example is explained in which, as the process of being bundled in the spatial units, the pieces of first projection data are added together from the plurality of detecting elements that are positioned adjacent to each other in the channel direction and the row direction of the photon counting detector; however, possible embodiments are not limited to this example. For instance, the second projection data generating function 372 may add together, as the bundling in the spatial units, at least one selected from between: pieces of first projection data from a plurality of detecting elements that are positioned adjacent to each other in the channel direction; and pieces of first projection data from a plurality of detecting elements that are positioned adjacent to each other in the row direction, in the photon counting detector.

More specifically, as the bundling in the spatial units, the second projection data generating function 372 may add together the pieces of first projection data from the plurality of detecting elements positioned adjacent to each other in the channel direction of the photon counting detector. Alternatively, as the bundling in the spatial units, the second projection data generating function 372 may add together the pieces of first projection data from the plurality of detecting elements positioned adjacent to each other in the row direction of the photon counting detector.

Figure 8:
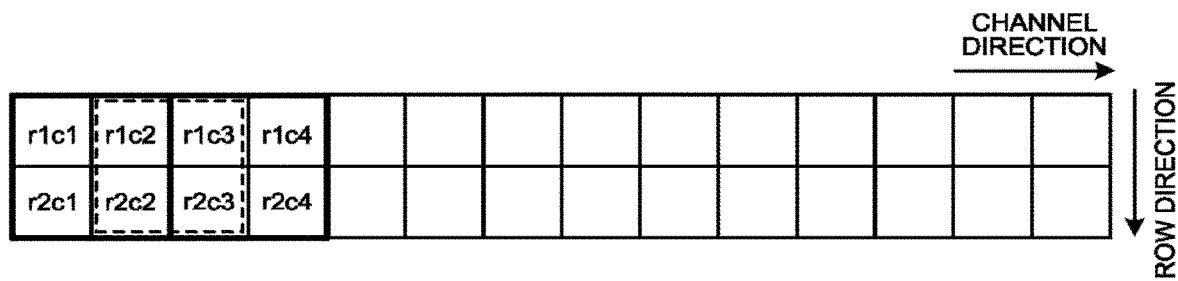

Further, in the embodiments described above, the example is explained in which the pieces of data are simply added together; however, possible embodiments are not limited to this example. For instance, the second projection data generating function 372 may generate second projection data by calculating a moving average of the pieces of first projection data. FIG. 8 is a drawing for explaining a modification example of the first embodiment.

FIG. 8 illustrates a part of the detecting elements included in the K-ray detector 13. Further, FIG. 8 illustrates the channel direction and the row direction. For the sake of convenience in the explanation, FIG. illustrates a group of 14×2 detecting elements, with fourteen detecting elements arranged in the channel direction and two detecting elements arranged in the row direction. However, the array pattern of the detecting elements in the channel direction and the row direction in the group of detecting elements according to possible embodiments are not limited to the one in this example and may arbitrarily be changed.

With reference to the example illustrated in FIG. 8, an example will be explained in which, as the bundling in the spatial units, the second projection data generating function 372 adds together pieces of first projection data from the plurality of detecting elements positioned adjacent to each other in the channel direction and the row direction in the photon counting detector. With respect to the group of 14×2 detecting elements illustrated in FIG. 8, the second projection data generating function 372 forms a group each made up of four detecting elements corresponding to 2×2 pixels. In this situation, the second projection data generating function 372 calculates a moving average so that pieces of first projection data from a part of the detecting elements are duplicate. In other words, the second projection data generating function 372 bundles together the group of 14×2 detecting elements into spatial units so as to form thirteen groups in the channel direction and one group in the row direction.

More specifically, the second projection data generating function 372 adds together the pieces of first projection data from the detecting elements $r1c1$, $r1c2$, $r2c1$, and $r2c2$ illustrated in FIG. 8. Subsequently, the second projection data generating function 372 adds together the pieces of first projection data from the detecting elements $r1c2$, $r1c3$, $r2c2$, and $r2c3$ illustrated in FIG. 8. After that, the second projection data generating function 372 adds together the pieces of first projection data from the detecting elements $r1c3$, $r1c4$, $r2c3$, and $r2c4$ illustrated in FIG. 8. In this manner, the second projection data generating function 372 generates the second projection data by calculating the moving average so that the pieces of first projection data from a part of the detecting elements are duplicate.

Alternatively, the second projection data generating function 372 may generate second projection data by performing a weighted addition on the pieces of first projection data in units each made up of a predetermined number of detecting elements. For example, the second projection data generating function 372 may perform the weighted addition by using a Point Spread Function (PSF).

Second Embodiment

In the embodiments described above, the example is explained in which, as the process of being bundled in the spatial units, at least one selected from between: the pieces of first projection data from the plurality of detecting elements positioned adjacent to each other in the channel direction; and the pieces of first projection data from the plurality of detecting elements Positioned adjacent to each other in the row direction, in the photon counting detector, are added together. In a second embodiment, an example will be explained in which, as the process of being bundled in spatial units, pieces of first projection data from detecting elements in mutually the same position in the photon counting detector are added together in units of views next to each other.

The configuration of the X-ray CT apparatus 1 according to the second embodiment is the same as that of the X-ray CT apparatus 1 illustrated in FIG. 1, except that a part of the second projection data generating function 372 is different. For this reason, in the second embodiment, only certain functions executed by the second projection data generating function 372 will be explained.

As the bundling in the spatial units, the second projection data generating function 372 is configured to add together the pieces of first projection data from the detecting elements in mutually the same position in the photon counting detector, in units of views next to each other. FIG. 9 is a drawing for explaining the second embodiment.

FIG. 9 illustrates a part of the detecting elements included in the X-ray detector 13. Further, the top section of FIG. 9 illustrates a group of detecting elements in an i-th view. The bottom section of FIG. 9 illustrates a group of detecting elements in an (i+1)-th view. Further, FIG. 9 illustrates the channel direction and the row direction. For the sake of convenience in the explanation, FIG. 9 illustrates a group of 14×4 detecting elements, with fourteen detecting elements arranged in the channel direction and four detecting elements arranged in the row direction. However, the array pattern of the detecting elements in the channel direction and the row direction in the group of detecting elements according to possible embodiments are not limited to the one in this example and may arbitrarily be changed.

As illustrated in FIG. 9, the second projection data generating function 372 bundles together, as one group, the detecting element $r1c1$ in the i-th view and the detecting element $r1c1$ in the (i+1)-th view. Further, as illustrated in FIG. 9, the second projection data generating function 372 similarly bundles together, as another group, the detecting element $r1c2$ in the i-th view and the detecting element $r1c2$ in the (i+1)-th view.

After that, the second projection data generating function 372 adds together the pieces of first projection data in each of the bundled groups. For example, the second projection data generating function 372 generates second projection data by adding together the numbers of photons in the X-rays corresponding to each of the energy bins from the piece of first projection data from the detecting element $r1c1$ in the i-th view and the piece of first projection data from the detecting element $r1c1$ in the (i+1)-th view illustrated in FIG. 9. In this situation, the second projection data generating function 372 simply adds together the numbers of photons from the detecting elements corresponding to each of the energy bins. After that, the reconstruction processing function 374 reconstructs a material decomposition image on the basis of the second projection data.

As explained above, in the second embodiment, as the process of being bundled in the spatial units, the pieces of first projection data from the detecting elements in mutually the same position in the photon counting detector are added together in units of views that are next to each other. As a result, according to the second embodiment, because the statistic amounts of the numbers of photons corresponding the energy bins are larger, the level of precision of the material decomposition process is improved.

In the second embodiment, the example is explained in which the pieces of first projection data are bundled together in units of views next to each other; however, possible embodiments are not limited to this example. For instance, the second projection data generating function 372 may use both the method of bundling in the spatial units explained in the first embodiment and the method of bundling in the spatial units explained in the second embodiment. More specifically, the second projection data generating function 372 may bundle together the pieces of first projection data in the channel direction, and also, in units of views next to each other. Alternatively, the second projection data generating function 372 may bundle together the pieces of first projection data in the now direction, and also, in units of views next to each other. In another example, the second projection data generating function 372 may bundle together the pieces of first projection data in the channel direction and the row direction, and also, in units of views next to each other.

Further, the example is explained in which the second projection data generating function 372 realizes the bundling process by simply adding together the pieces of first projection data; however, possible embodiments are not limited to this example. For instance, the second projection data generating function 372 may generate second projection data by calculating a moving average of the pieces of first projection data. Alternatively, the second projection data generating function 372 may generate second projection data by performing a weighted addition on the pieces of first projection data in units each made up of a predetermined number of detecting elements. For example, when performing a weighted addition among three views, the second projection data generating function 372 performs the weighted addition by applying a largest weight to the view in the middle.

Other Embodiments

Possible embodiments are not limited to the embodiments described above.

Further, in the embodiments above, the example is explained in which the second projection data generating function 372 generates the second projection data as being triggered by the start of the base image reconstruction process performed by the reconstruction processing function 374 or by the receipt of the first projection data from the data acquiring circuit 14. However, possible embodiments are not limited to this example. For instance, the second projection data generating function 372 may generate the second projection data only when the statistic amount of the first projection data is smaller than a certain criterion. More specifically, the second projection data generating function 372 may generate the second projection data when the number of photons is smaller than a threshold value (a first threshold value) in each of all the energy bins with respect to the first projection data. In that situation, it is acceptable to set a threshold value to be used in common to all the energy bins. Alternatively, it is also acceptable to set mutually-different threshold values among the energy bins. In another example, the second projection data generating function 372 may generate second projection data when the number of energy bins containing photons fewer than a threshold value is equal to or larger than a predetermined value or when the number of photons in a specific energy bin is smaller than a threshold value. In other words, the second projection data generating function 372 may generate the second projection data when the numbers of photons in the pieces of first projection data are smaller than a threshold value.

Further, when the number of photons in the first projection data is smaller than a second threshold value which is smaller than the first threshold value, the second projection data generating function 372 may increase the number of X-ray detecting elements belonging to each of the groups used as the units or the bundling process. FIG. 10 is a drawing for explaining an example of the process performed when the number of photons is smaller than the second threshold value. For example, as illustrated in FIG. 10, when the number of photons in the first projection data is smaller than the first threshold value, but is equal to or larger than the second threshold value, the second projection data generating function 372 forms each group with four detecting elements corresponding to 2×2 pixels. In contrast, when the number of photons in the first projection data is smaller than the second threshold value, the second projection data generating function 372 forms each group with sixteen detecting elements corresponding to 4×4 pixels. In other words, the second projection data generating function 372 may change the units used for the bundling process, in accordance with the numbers of photons in the pieces of first projection data.

Further, there is a tendency that the number of photons derived from X-rays that have passed through a thinner part of a subject is larger than the number of photons derived from X-rays that have passed through a thicker part of the subject. Thus, attenuation of X-rays varies depending on the section of the subject through which X-rays pass. Accordingly, the second projection data generating function 372 may generate second projection data by bundling together, in spatial units, only pieces of first projection data output from X-ray detecting elements detecting X-rays passing through such a part that has a thickness equal to or smaller than a threshold value, within the sections of the subject through which X-rays pass. Alternatively, the second projection data generating function 372 may generate the second projection data by bundling together, in spatial units, only pieces of the first projection data output from the X-ray detecting elements detecting X-rays passing through such a part that has X-ray attenuation predicted from the thickness of the section of the subject equal to or greater than the threshold, within the sections of the subject through which the X-rays pass. A second projection data generating process according to this modification example will be explained, with reference to FIG. 11.

FIG. 11 is a flowchart illustrating an exemplary flow in the second projection data generating process according to the modification example. The second projection data generating process according to the present modification example is performed for each of the views. For example, as illustrated in FIG. 11, the second projection data generating function 372 obtains subject information indicating the physique of the subject stored in the storage circuitry 35 (step S20). The subject whose physique is indicated in the subject information obtained at step S20 is the subject from which the first projection data serving as a processing target has been acquired. After that, the second projection data generating function 372 derives the thickness of the section of the subject through which X-rays pass, by using the subject information (step S21).

Subsequently, from among the plurality of X-ray detecting elements, the second projection data generating function 372 identifies the X-ray detecting elements detecting X-rays passing through such a part of which the derived thickness is equal to or larger than a threshold value (a third threshold value) (step S22). After that, the second projection data generating function 372 generates second projection data by bundling together, in the spatial units, only the pieces of first projection data output from the identified X-ray detecting elements (step S23) and thus ends the second projection data generating process.

As a result of the second projection data generating process performed in this manner, the second projection data is generated for each of the views on the basis of the pieces of first projection data only from such X-ray detecting elements that are expected to have a small number of photons, on the basis of the subject information. After that, the reconstruction processing function 374 reconstructs CT image data by using, for example, projection data from the entire circumference (corresponding to 360 degrees) (the second projection data for the entire circumference and the projection data for the entire circumference from the X-ray detecting elements detecting X-rays passing through such a part of which the thickness is smaller than the threshold value).

Alternatively, the second projection data generating function 372 may judge whether or not the number of photons is smaller than the threshold value in each of all the energy bins in the first projection data, by using projection data acquired at the time of taking a position determining image as the first projection data. After that, when the number of photons is smaller than the threshold value in each of all the energy bins, the second projection data generating function 372 may generate, as second projection data, data obtained by bundling together, in spatial unit, pieces of projection data acquired during a main image taking process.

Further, when the reconstruction processing function 374 obtains the material decomposition information, the material decomposition process may be performed on either projection data or image data.

In the embodiments described above, the example is explained while using the X-ray CT apparatus 1 of a rotate/rotate type (third-generation CT) in which the X-ray tube 12a and the X-ray detector 13 rotate around the subject while being integrally structured with each other; however, possible embodiments are not limited to this example. For instance, besides the third-generation CT, other examples of X-ray CT apparatuses include those of a stationary/rotary type (fourth-generation CT) in which an X-ray detector including a plurality of X-ray detecting elements is fixed in a ring formation in a distributed manner so that only an X-ray tube rotates around the subject. The embodiments described above are also applicable to the fourth-generation CT. In addition, the embodiments described above are also applicable to hybrid X-ray CT apparatuses in which the third-generation CT and the fourth-generation CT are combined together.

Further, the embodiments described above are also applicable to conventional X-ray CT apparatuses of single tube types and to X-ray CT apparatuses of multiple tube types in which a plurality of pairs each made up of an X-ray tube and a detector are installed on a rotating ring.

Further, in the embodiments above, the example is explained in which the processing circuitry 37 performs the plurality of functions; however, possible embodiments are not limited to this example. For instance, another arrangement is acceptable in which the plurality of functions are provided as independent circuits in the console 30, so that each of the circuits executes the function thereof. For instance, the second projection data generating function 372 executed by the processing circuitry 37 may be provided as a second projection data generating circuit, so that the second projection data generating circuit executes the second projection data generating function. Further, the reconstruction processing function 374 executed by the processing circuitry 37 may be provided as reconstruction processing circuitry, so that the reconstruction processing circuitry executes the reconstruction processing function.

Further, in the embodiments above, the example is explained in which the second projection data generating function 372 and the reconstruction processing function 374 are executed in the console 30; however, possible embodiments are not limited to this example. For instance, the second projection data generating function 372 and the reconstruction processing function 374 may be executed in an external workstation.

Further, the material decomposition process explained in the embodiments above may be realized with software. For example, the material decomposition process may be realized by causing a computer to execute a material decomposition program defining the procedures in the processes that were explained as being performed by the second projection data generating function 372 and the reconstruction processing function 374 in the embodiments above. The material decomposition program may be stored, for example, in a hard disk, a semiconductor memory element, or the like, so as to be read and executed by a processor such as a Central Processing Unit. (CPU), a Micro Processing Unit (MPU), or the like. Further, the material decomposition program may be distributed as being recorded on a computer-readable recording medium such as a Compact Disk Read-Only Memory (CD-ROM), a Magnetic Optical (MO) disk, a Digital Versatile Disk (DVD), or the like.

The term "processor" used in the above explanation denotes, for example, a Central Processing Unit (CPU), a Graphics Processing Unit (GPU), or a circuit such as an Application Specific integrated Circuit (ASIC) or a programmable logic device (e.g., a Simple Programmable Logic Device [SFLD], a Complex Programmable Logic Device [CPLD], or a Field Programmable Gate Array [FPGA]). The one or more processors realize the functions thereof by reading and executing the programs incorporated in the circuits thereof. Instead of incorporating the programs into the circuits of the processors, it is also acceptable to store the programs into a storage circuitry included in the console 30. In that situation, the one or more processors realize the functions thereof by reading and executing the programs stored in the storage circuitry. The processors in the present embodiments do not each necessarily have to be structured as a single circuit. It is also acceptable to structure one processor by combining together a plurality of independent circuits so as to realize the functions thereof. Further, it is also acceptable to incorporate two or more of the constituent elements illustrated in FIG. 1 into one processor so as realize the functions thereof.

In the explanations of the embodiments above, the constituent elements of the apparatuses and the devices illustrated in the drawings are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a computer program analyzed and executed by the CPU or may be realized as hardware using wired logic.

It is possible to realize the controlling methods described in the embodiments above by causing a controlling computer program (hereinafter, "controlling program") prepared in advance to be executed by a computer such as a personal computer, a workstation, or the like. The controlling program may be distributed via a network such as the Internet. Further, the controlling program may be recorded onto a computer-readable recording medium such as a hard disk, a flexible disk (FD), a Compact Disk Read-Only Memory (CD-ROM), a magnetic-optical (MO) disk, a Digital Versatile Disk (DVD), or the like, so as to be executed as being read from the recording medium by a computer.

According to at least one aspect of the embodiments described above, it is possible to realize a high material decomposition capability.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
a photon counting detector that includes a plurality of detecting elements each of which is configured to output signals corresponding to numbers of photons that are counted; and
processing circuitry configured to generate pieces of first projection data on a basis of the signals from the plurality of detecting elements, to generate second projection data by bundling together, in spatial units, pieces of first projection data from a predetermined number of detecting elements among the plurality of detecting elements, and to reconstruct a material decomposition image on a basis of the second projection data, wherein, as the bundling in the spatial units, the processing circuitry adds together the pieces of first projection data from detecting elements in a mutually same position in the photon counting detector, in units of views next to each other.

2. The X-ray CT apparatus according to claim 1, wherein, as the bundling in the spatial units, the processing circuitry adds together pieces of first projection data from two or more of the detecting elements positioned adjacent to each other in a channel direction in the photon counting detector.

3. The X-ray CT apparatus according to claim 1, wherein, as the bundling in the spatial units, the processing circuitry adds together pieces of first projection data from two or more of the detecting elements positioned adjacent to each other in a row direction in the photon counting detector.

4. The X-ray CT apparatus according to claim 1, wherein, as the bundling in the spatial units, the processing circuitry adds together pieces of first projection data from two or more of the detecting elements positioned adjacent to each other in a channel direction and in a row direction in the photon counting detector.

5. The X-ray CT apparatus according to claim 1, wherein the processing circuitry generates the second projection data by calculating a moving average of the pieces of first projection data.

6. The X-ray CT apparatus according to claim 1, wherein the processing circuitry generates the second projection data by performing a weighted addition on the pieces of first projection data in units each made up of a predetermined number of detecting elements among the plurality of detecting elements.

7. The X-ray CT apparatus according to claim 1, wherein
the processing circuitry further generates a base image on a basis of the pieces of first projection data, each of the pieces of first projection data indicating the number of photons in each of a plurality of energy bins,
the processing circuitry generates images based on the second projection data respectively corresponding to the plurality of energy bins,
the processing circuitry generates final images respectively corresponding to the energy bins using the base image and the images generated based on the second projection data, the final images having higher spatial resolution than the images that are generated based on the second projection data, and
the processing circuitry reconstructs the material decomposition image by using a result of performing a material decomposition process on the generated final images corresponding to the energy bins.

8. The X-ray CT apparatus according to claim 1, wherein the processing circuitry generates the second projection data when the numbers of photons in the pieces of first projection data are smaller than a threshold value.

9. The X-ray CT apparatus according to claim 1, wherein the processing circuitry changes the units used for the bundling, in accordance with the numbers of photons in the pieces of first projection data.

10. The X-ray CT apparatus according to claim 1, wherein
the processing circuitry calculates, for each of the plurality of detecting elements, attenuation of X-rays passing through a subject, based on subject information indicating a physique of the subject, and
from among the plurality of detecting elements, the processing circuitry generates the second projection data by bundling together, in the spatial units, only pieces of first projection data output from detecting elements detecting X-rays passing through such a part of the subject of which the calculated attenuation is equal to or larger than a threshold value.

11. An X-ray CT apparatus comprising:
a photon counting detector that includes a plurality of detecting elements each of which is configured to output signals corresponding to numbers of photons that are counted; and
processing circuitry configured to generate pieces of first projection data on a basis of the signals from the plurality of detecting elements, to generate second projection data by bundling together, in spatial units, pieces of first projection data from a predetermined number of detecting elements among the plurality of detecting elements, and to reconstruct a material decomposition image on a basis of the second projection data,
wherein the processing circuitry changes the units used for the bundling, in accordance with the numbers of photons in the pieces of first projection data.

12. The X-ray CT apparatus according to claim 11, wherein, as the bundling in the spatial units, the processing circuitry adds together pieces of first projection data from two or more of the detecting elements positioned adjacent to each other in a channel direction in the photon counting detector.

13. The X-ray CT apparatus according to claim 11, wherein, as the bundling in the spatial units, the processing circuitry adds together pieces of first projection data from two or more of the detecting elements positioned adjacent to each other in a row direction in the photon counting detector.

14. The X-ray CT apparatus according to claim 11, wherein, as the bundling in the spatial units, the processing circuitry adds together pieces of first projection data from two or more of the detecting elements positioned adjacent to each other in a channel direction and in a row direction in the photon counting detector.

15. An X-ray CT apparatus comprising:
   a photon counting detector that includes a plurality of detecting elements each of which is configured to output signals corresponding to numbers of photons that are counted; and
   processing circuitry configured to generate pieces of first projection data on a basis of the signals from the plurality of detecting elements, to generate second projection data by bundling together, in spatial units, pieces of first projection data from a predetermined number of detecting elements among the plurality of detecting elements, and to reconstruct a material decomposition image on a basis of the second projection data,
   wherein the processing circuitry calculates, for each of the plurality of detecting elements, attenuation of X-rays passing through a subject, based on subject information indicating a physique of the subject, and
   wherein from among the plurality of detecting elements, the processing circuitry generates the second projection data by bundling together, in the spatial units, only pieces of first projection data output from detecting elements detecting X-rays passing through such a part of the subject of which the calculated attenuation is equal to or larger than a threshold value.

16. The X-ray CT apparatus according to claim 15, wherein, as the bundling in the spatial units, the processing circuitry adds together pieces of first projection data from two or more of the detecting elements positioned adjacent to each other in a channel direction in the photon counting detector.

17. The X-ray CT apparatus according to claim 15, wherein, as the bundling in the spatial units, the processing circuitry adds together pieces of first projection data from two or more of the detecting elements positioned adjacent to each other in a row direction in the photon counting detector.

18. The X-ray CT apparatus according to claim 15, wherein, as the bundling in the spatial units, the processing circuitry adds together pieces of first projection data from two or more of the detecting elements positioned adjacent to each other in a channel direction and in a row direction in the photon counting detector.

* * * * *